US00PP09282P

United States Patent [19]

Kahl et al.

[11] Patent Number: Plant 9,282

[45] Date of Patent: Sep. 12, 1995

[54] ALMOND TREE (KAHL)

[76] Inventors: Marvin Kahl, 8729 E. Mariposa Way; Kitt Kahl, 2074 S. Whealan Rd., both of Merced, Calif. 95340

[21] Appl. No.: 237,768

[22] Filed: May 4, 1994

[51] Int. Cl.[6] ..... A01H 5/00

[52] U.S. Cl. ..... Plt./32.2

[58] Field of Search ..... Plt. 32.2

[56] References Cited

U.S. PATENT DOCUMENTS

P.P. 2,641 6/1966 Arakaki ..... Plt./32.2

*Primary Examiner*—James R. Feyrer

[57] ABSTRACT

The present invention relates to an almond tree and more particularly to a new and distinct variety broadly characterized by a medium size, vigorous, upright, hardy, very productive, and regular bearing tree whose nuts mature under the ecological conditions described approximately the third week in September. The nuts are very well sealed to protect kernels that are uniformly large in size, brown in color, and flat in shape.

1 Drawing Sheet

BACKGROUND OF THE VARIETY

For the past 50 years the Kahl family has grown almonds commercially in California. During that time we have farmed many different varieties of almonds and have had many chance seedlings sprout and grow into young trees. Sometimes these seedlings were transplanted and grafted to standard varieties, but occasionally one would escape grafting, bear a heavy crop of nuts at an early age, and be kept for further evaluation as a potential commercial variety. One such chance seedling sprouted in our orchard in 1972 and survived our evaluation to become a mature tree.

The present invention relates to a new and distinct variety of almond tree, which has been denominated varietally as "Kahl". The present variety was selected by us in a cultivated area of our experimental orchard at near Le Grand, Calif. in Merced County (San Joaquin Valley). This seedling resulted as a chance seedling in a Nonpareil (unpatented), Davey (unpatented), and Mission (unpatented) planting. Subsequent to origination of the present variety of almond tree, we asexually reproduced it by budding and grafting in the same experimental orchard identified above, and such reproduction of plant and nut characteristics were true to the original plant in all respects.

We originally tested and selected the present variety because of its heavy production and its potential to pollinate Nonpareil, blooming about 3 days later than Nonpareil. With the emergence of the Carmel (U.S. Plant Pat. No. 2,641) as a prominent commercial variety of California, the value of the present variety as a pollinator and co-planter with both Nonpareil and Carmel is substantial.

The present almond variety is most similar to Carmel (U.S. Plant Pat. No. 2,641) by being an early blooming variety that abundantly produces large almonds that harvest after Nonpareil (unpatented), but is distinguished therefrom and an improvement thereon by appearing to be free of budfailure, by being a much larger and more vigorous tree, by harvesting one week earlier, by having a pink blossom instead of white, and by being interfertile with both Nonpareil and Carmel.

DRAWING

The accompanying color photograph exhibits nuts in hull, nuts out of hull, kernels out of shell, and leaves, all typical of the instant variety.

POMOLOGICAL CHARACTERISTICS

Referring now more specifically to the pomological characteristics of this new and distinct variety of almond tree, the following has been observed under the ecological conditions prevailing near Le Grand, Merced County (San Joaquin Valley), Calif., and was developed at the harvest stage on Sept. 13, 1993. All major color code designations are by reference to the Inter-Society Color Council, National Bureau of Standards. Common color names are also used occasionally.

TREE

Size: Medium.
Vigor: Vigorous.
Growth: Upright and dense.
Form: Vase formed and round topped.
Hardiness: Hardy.
Production: Very productive.
Bearing: Regular bearer.
Trunk:
- *Size.*—Medium.
- *Texture.*—Medium.
- *Bark color.*—Brownish gray [64. brGy].
- *Lenticels.*—Numerous. Color: Dark orange yellow [72. d.OY]. Average Size: $\frac{1}{4}''$ [6.4 mm.].

Branches:
- *Size.*—Medium.
- *Texture.*—Smooth.
- *Color.*—1st Year Wood: Moderate yellow green [120. m.YG]. Older Wood: Moderate brown [58. m.Br].
- *Lenticels.*—Numerous, very small.

Leaves:
- *Size.*—Medium. Average length: 3 $\frac{7}{8}''$ [98.4 mm.]. Average width: 1 $\frac{1}{8}''$ [28.6 mm.].
- *Thickness.*—Medium.
- *Form.*—Elliptical.
- *Apex.*—Acuminate.

*Base.*—Acute.
*Surface.*—Smooth.
*Color.*—Dorsal surface: Moderate olive green [125. m.OlG]. Ventral surface: Moderate yellow green [120. m.YG].
*Margin.*—Serrate.
*Venation.*—Pinnately net veined.
*Petiole.*—Average length: 1 ⅛" [28.6 mm.]. Average thickness: 1/16" [1.6 mm.]. Dorsal color: Moderate yellow green [120. m.YG]. Ventral color: Light yellow green [119. l.YG].
*Stipules.*—Few. Average length: 5/32" [4.0 mm.].
*Glands.*—Numbers: Mostly 2 to 4 per leaf. Position: Mostly alternately positioned on petiole. Size: Small. Form: Globose. Color: Grayish reddish orange [39. gy.rO].

Flower buds:
*Hardiness.*—Hardy.
*Size.*—Large.
*Length.*—Large.
*Form.*—Free.
*Surface.*—Pubescent.

Flowers:
*Blooming period.*—Approximately 3 days later than Nonpareil.
*Blooming duration.*—Medium.
*Type.*—Self-sterile, must be cross pollinated by other varieties.
*Amount of bloom.*—Heavy.
*Size.*—Large.
*Color.*—Pale pink [7. p.Pk].

HULL

Outer surface: Smooth, Pubescent.
Form: Uniform, symmetrical.
*Longitudinal section form.*—Oval.
Average Thickness: 3/32" to ⅛" [2.4–3.2 mm.].
Flesh: Tough.
Suture: A sharp crack prior to splitting.
External color: Light brownish gray [63. l.brGy] when dry.
Dehiscence: Opens freely.
Splitting: Complete along suture.
Adherence: Hulls are easily removed from nuts by mechanical hullers.
Density: Hulls are dense and tough, stay intact, and can be readily skimmed by mechanical classifiers during hulling and shelling processes.
Nut cavity: Oblong.
*Surface.*—Rough.
*Color when first opened.*—Pale yellow green [121. p.YG].
*Color when dry.*—Strong yellowish brown [74. s.yBr].

NUT

Size:
*Average length.*—1 ½" [38.1 mm.].
*Average width.*—¾" [19.1 mm.].
*Average thickness.*—⅝" [15.9 mm.].
*Average weight.*—9.65 nuts per ounce [2.94 grams per nut].
Form: Oval.
Shell:
*Color.*—Light yellowish brown [76. l.yBr].
*Average wall thickness.*—⅛" [3.2 mm.].
*Pits.*—Small, numerous.
*Outer shell.*—Crumbling.
*Inner shell.*—Thin, brittle, well sealed.
Base: Slightly oblique.
Apex: Acute.
Stem: Medium.
*Average length.*—¼" [6.4 mm.].
*Average diameter.*—3/16" [4.8 mm.].
Wing: Thin, extended toward apex.
*Maximum protrusion.*—⅛" [3.2 mm.].
Inner surface: Smooth.
*Color.*—Moderate orange yellow [71. m.OY].

KERNEL

Size: Medium to large.
*Average length.*—1 ⅛" [28.6 mm.].
*Average width.*—½" [12.7 mm.].
*Average thickness.*—5/16" [7.9 mm.].
*Average weight.*—18.4 nuts per ounce [1.54 grams per nut].
Form: Mostly symmetrical, with some variation due to doubles or aborted doubles.
*Longitudinal section form.*—Ovate.
*Transverse section form.*—Elliptically flattened.
Base: Oblique.
Apex: Acute to somewhat acuminate.
Surface: Slightly wrinkled, very slight pubescence.
*Skin color.*—Strong yellowish brown [74. s.yBr].
*Pellicle color.*—Grayish yellowish brown [80. gy-.yBr].
*Veins.*—Numerous moderate yellowish brown [77. m.yBr] veins extending longitudinally from the pellicle to the apex with some branching.
Number of doubles: Moderate to numerous.
Number of defective kernels: Very few on most years.
Flavor: Mild and slightly sweet.
Astringency: None.
Quality: Good.
Viable: Yes.
Blanchable: Yes.
Percentage of kernel to nut: 52%.

CULTURAL CHARACTERISTICS

Resistance to insects: Much more resistant to kernel insect damage than Nonpareil due to its very well sealed inner shell.
Susceptibility to budfailure: None observed.
Resistance to other diseases: No unusual susceptibilities noted.
Susceptibility to frost: No unusual susceptibility noted.

Although the new variety of almond tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of almond tree, substantially as illustrated and described, which is most similar to the Carmel (U.S. Plant Pat. No. 2,641) by being an early blooming variety that abundantly produces large, flat kernels that harvest after Nonpareil, but is distinguished therefrom and an improvement thereon by appearing to be free of budfailure, by being a much larger and more vigorous tree, by harvesting one week earlier, and by having a pink blossom instead of white.

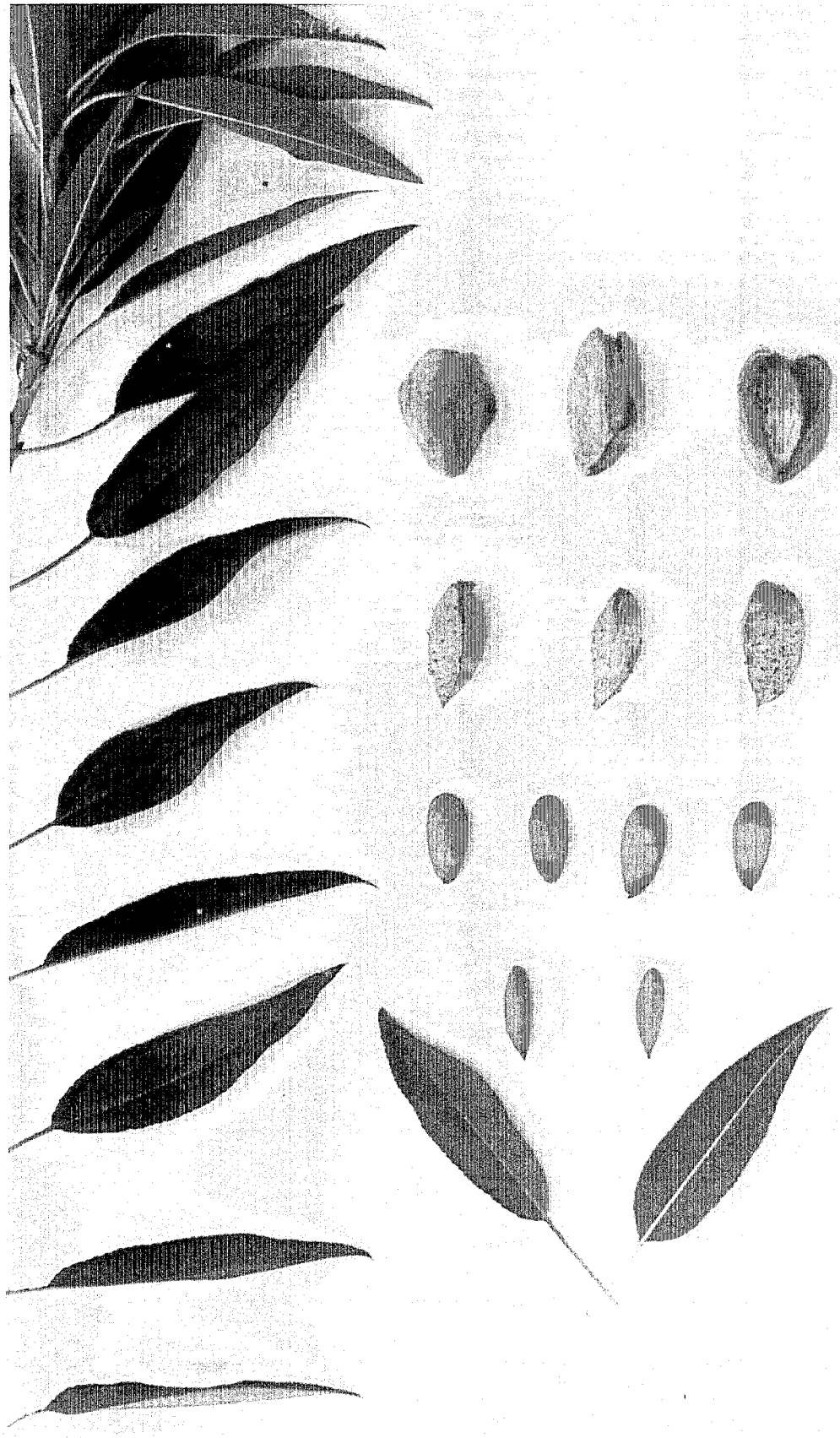

* * * * *